US011454144B1

(12) United States Patent
Kennedy et al.

(10) Patent No.: US 11,454,144 B1
(45) Date of Patent: Sep. 27, 2022

(54) LUBRICANT DILUTION DETECTION SYSTEM

(71) Applicant: Caterpillar Inc., Peoria, IL (US)

(72) Inventors: Joseph L. Kennedy, Zionsville, IN (US); Michael J. Campagna, Chillicothe, IL (US); Andrew W. Billing, Bloomington, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 17/211,388

(22) Filed: Mar. 24, 2021

(51) Int. Cl.
| | |
|---|---|
| F01M 1/18 | (2006.01) |
| G01N 33/28 | (2006.01) |
| F01M 11/10 | (2006.01) |
| F01M 1/16 | (2006.01) |

(52) U.S. Cl.
CPC ............. *F01M 1/18* (2013.01); *F01M 11/10* (2013.01); *G01N 33/2835* (2013.01); *G01N 33/2841* (2013.01); *G01N 33/2847* (2013.01); *G01N 33/2888* (2013.01); *F01M 2001/165* (2013.01); *F01M 2011/142* (2013.01); *F01M 2011/1446* (2013.01); *F01M 2011/1473* (2013.01); *F02D 2250/11* (2013.01)

(58) Field of Classification Search
CPC .............................................. F01M 2001/165
See application file for complete search history.

(56) References Cited

U.S. PATENT DOCUMENTS

| | | |
|---|---|---|
| 3,411,313 A | 11/1968 | Brown |
| 5,320,196 A | 6/1994 | Mouton |
| 6,966,304 B2 * | 11/2005 | Nagaishi ............... F02D 35/025 123/480 |
| 7,260,982 B2 * | 8/2007 | Utz ........................ F02M 65/00 73/114.55 |
| 8,109,138 B2 * | 2/2012 | Han ....................... G01N 11/06 73/114.55 |
| 8,734,122 B2 | 5/2014 | Murray et al. |
| 9,394,843 B2 * | 7/2016 | Hakeem ............. F02D 41/0007 |
| 9,470,173 B2 * | 10/2016 | Lehmen ............... F02D 41/064 |
| 9,726,129 B2 * | 8/2017 | Pfeiffer ................. F02M 59/20 |

(Continued)

FOREIGN PATENT DOCUMENTS

| | | | | |
|---|---|---|---|---|
| CN | 102216572 A | * | 10/2011 | ............... F01M 1/10 |
| CN | 102216572 B | * | 7/2013 | ............... F01M 1/10 |

(Continued)

OTHER PUBLICATIONS

Written Opinion and International Search Report for Int'l. Patent Appln. No. PCT/US2022/019145, dated Jun. 23, 2022 (11 pgs).

*Primary Examiner* — Kevin R Steckbauer
(74) *Attorney, Agent, or Firm* — Bookoff McAndrews, PLLC (57) ABSTRACT

Lubricant dilution detection systems and methods are disclosed. A method for detecting lubricant dilution for a lubrication system includes detecting a shutdown event of the lubrication system. The method includes measuring lubricant pressure during the shutdown event. The method further includes determining lubricant dilution based on the measured lubricant pressure during the shutdown event. In accordance with a determination that there is lubricant dilution, the method includes outputting an indication of the lubricant dilution.

20 Claims, 5 Drawing Sheets

(56) References Cited

U.S. PATENT DOCUMENTS

| | | | |
|---|---|---|---|
| 10,107,212 B2 * | 10/2018 | Kittaka | F02D 19/0655 |
| 10,202,911 B2 | 2/2019 | Cunningham et al. | |
| 10,233,799 B2 * | 3/2019 | Ogata | F02D 35/026 |
| 10,323,596 B2 * | 6/2019 | Miyamoto | F02D 41/2454 |
| 11,261,766 B1 * | 3/2022 | Dudar | F01M 13/0011 |
| 2004/0099252 A1 * | 5/2004 | Nagaishi | F02D 41/22 123/480 |
| 2006/0037387 A1 * | 2/2006 | Utz | F02M 65/00 73/114.55 |
| 2012/0042845 A1 * | 2/2012 | Kanai | F01M 1/10 123/196 AB |
| 2014/0174408 A1 * | 6/2014 | Pfeiffer | F01M 1/18 123/496 |
| 2015/0369157 A1 * | 12/2015 | Lehmen | F02D 41/064 701/105 |
| 2016/0102623 A1 * | 4/2016 | Hakeem | F01M 5/04 701/113 |
| 2018/0246010 A1 | 8/2018 | Bachmann | |
| 2019/0093583 A1 * | 3/2019 | Miyamoto | F02D 41/1456 |
| 2019/0195095 A1 | 6/2019 | Dudar | |

FOREIGN PATENT DOCUMENTS

| | | | | |
|---|---|---|---|---|
| CN | 103883375 A | * | 6/2014 | F01M 1/18 |
| CN | 105240087 A | * | 1/2016 | F02D 41/064 |
| CN | 105507983 A | * | 4/2016 | F01M 5/02 |
| CN | 107110043 A | * | 8/2017 | F01M 13/022 |
| CN | 103883375 B | * | 9/2017 | F01M 1/18 |
| CN | 108506114 A | * | 9/2018 | F01M 11/10 |
| CN | 108506114 A | | 9/2018 | |
| CN | 105240087 B | * | 3/2019 | F02D 41/064 |
| CN | 105507983 B | * | 11/2019 | F01M 5/02 |
| CN | 107110043 B | * | 4/2020 | F01M 13/022 |
| CN | 214667498 U | * | 11/2021 | F01M 11/10 |
| CN | 114270019 A | * | 4/2022 | F01M 11/10 |
| DE | 10055420 A1 | * | 5/2002 | F01M 11/10 |
| DE | 10306857 A1 | * | 9/2004 | F01M 11/10 |
| DE | 102004039836 A1 | * | 3/2006 | F01M 11/10 |
| DE | 102006059071 A | * | 6/2008 | G01N 33/2888 |
| DE | 102009046417 A1 | * | 5/2011 | F01M 13/00 |
| DE | DE-102012112794 A1 | * | 6/2014 | F01M 1/18 |
| DE | 102014013709 A1 | * | 3/2015 | F01M 1/16 |
| DE | 102014216701 A1 | * | 3/2015 | B60K 6/445 |
| DE | 102015108997 A1 | * | 12/2015 | F02D 41/064 |
| DE | 102015117117 A1 | * | 4/2016 | F01M 5/02 |
| DE | 102004039836 B4 | * | 6/2016 | F01M 11/10 |
| DE | 102019002381 A1 | * | 10/2020 | F01M 11/10 |
| DE | 102019213123 B3 | * | 1/2021 | F01M 11/10 |
| DE | 102020003121 A1 | * | 11/2021 | F01M 11/10 |
| DE | 102020126900 A1 | * | 4/2022 | F01M 11/10 |
| EP | 2395209 A1 | * | 12/2011 | F01M 1/10 |
| FR | 2874404 A1 | * | 2/2006 | F01M 11/10 |
| FR | 2974853 A1 | * | 11/2012 | F01M 11/10 |
| FR | 3033440 A1 | * | 9/2016 | F01M 11/10 |
| GB | 2417291 A | * | 2/2006 | F01M 11/10 |
| JP | 2004137953 A | * | 5/2004 | F01M 11/10 |
| JP | 2004197591 A | * | 7/2004 | F02D 35/025 |
| JP | 2004522888 A | * | 7/2004 | F01M 11/10 |
| JP | 2004-293394 A | | 10/2004 | |
| JP | 2004278449 A | * | 10/2004 | F02D 19/084 |
| JP | 2004293394 A | * | 10/2004 | F01M 11/10 |
| JP | 2004340090 A | * | 12/2004 | F01M 11/10 |
| JP | 2006009597 A | * | 1/2006 | F01M 11/10 |
| JP | 4055545 B2 | * | 3/2008 | F01M 11/10 |
| JP | 4055568 B2 | * | 3/2008 | F02D 35/025 |
| JP | 4304489 B2 | * | 7/2009 | F01M 11/10 |
| JP | 4962625 B2 | * | 6/2012 | F01M 1/10 |
| JP | WO2010089890 A1 | * | 8/2012 | F01M 1/10 |
| JP | 2014-098360 A | | 5/2014 | |
| JP | 2014122626 A | * | 7/2014 | F01M 1/18 |
| JP | 2015168379 A | * | 9/2015 | F01M 11/10 |
| JP | 2016118147 A | * | 6/2016 | F01M 13/022 |
| JP | 6176159 B2 | | 7/2017 | |
| JP | 6176159 B2 | * | 8/2017 | F01M 11/10 |
| JP | 6375935 B2 | * | 8/2018 | F01M 13/022 |
| JP | 2019-147539 A | | 9/2019 | |
| JP | 2019147539 A | * | 9/2019 | F01M 1/10 |
| JP | 2019190288 A | | 10/2019 | |
| JP | 2020-133535 A | | 8/2020 | |
| JP | 2020133535 A | * | 8/2020 | F01M 11/10 |
| JP | 6965791 B2 | * | 11/2021 | F01M 11/10 |
| KR | 2300882 B1 | * | 9/2021 | F01M 11/10 |
| RU | 2692605 C2 | * | 6/2019 | F02D 41/064 |
| RU | 2701246 C2 | * | 9/2019 | F01M 5/02 |
| WO | WO-2006005649 A1 | * | 1/2006 | F01M 1/18 |
| WO | WO-2006005650 A1 | * | 1/2006 | F01M 1/18 |
| WO | WO-2006087489 A1 | * | 8/2006 | F01P 7/167 |
| WO | WO-2007028919 A1 | * | 3/2007 | F01M 11/10 |
| WO | 2008/071639 A1 | | 6/2008 | |
| WO | WO-2008071639 A1 | * | 6/2008 | G01N 33/2888 |
| WO | WO-2010089890 A1 | * | 8/2010 | F01M 1/10 |
| WO | WO-2016098278 A1 | * | 6/2016 | F01M 13/022 |
| WO | WO-2021037852 A1 | * | 3/2021 | F01M 11/10 |

* cited by examiner

LUBRICANT DILUTION DETECTION SYSTEM

TECHNICAL FIELD

The present disclosure relates generally to lubrication systems, and more particularly, to a lubricant dilution detection system for such lubrication systems.

BACKGROUND

Lubrication systems may provide one or more pressurized lubricants to various moving components (e.g., bearings, gears, etc.) to lubricate the components. Lubricants, such as oil, used in the lubrication systems may become diluted over time due to various causes. For example, liquid fuel (e.g., diesel fuel) from a fuel system of an engine and/or coolant from an oil cooler may leak into the lubrication system and become mixed with the lubricant. Consequently, the viscosity, and thus the lubrication ability, of the lubricant may be reduced. Accordingly, the moving components may become damaged over time due the diluted lubricant. Current methods for detecting lubricant dilution may require manually testing the lubricant using a sample of the lubricant and/or may not adequately detect dilution of the lubricant.

Japanese Patent Application Publication No. 2004293394, published on Oct. 21, 2004 ("the '394 publication"), describes an oil dilution prevention device for an engine. The oil dilution prevention device includes means for detecting a parameter relating to a dilution rate of the engine oil. The parameter can include pressure of the engine oil during an idling operation of the engine. The oil dilution prevention device of the '394 publication detects the engine oil is diluted when the pressure of the engine oil is equal to or less than a threshold value during the idling condition. However, the device of the '394 publication may not adequately detect lubricant dilution and/or may falsely diagnose dilution of the lubricant.

The lubricant dilution detection system of the present disclosure may solve one or more of the problems set forth above and/or other problems in the art. The scope of the current disclosure, however, is defined by the attached claims, and not by the ability to solve any specific problem.

SUMMARY

In one aspect, a method for detecting lubricant dilution for a lubrication system is disclosed. The method includes: detecting a shutdown event of the lubrication system; measuring lubricant pressure during the shutdown event; determining lubricant dilution based on the measured lubricant pressure during the shutdown event; and in accordance with a determination that there is lubricant dilution, outputting an indication of the lubricant dilution.

In another aspect, a lubricant dilution detection system is disclosed. The system includes: a lubrication system; a sensor for measuring lubricant pressure in the lubrication system; and a controller configured to: detect a shutdown event of the lubrication system; measure lubricant pressure during the shutdown event; determine lubricant dilution based on the measured lubricant pressure during the shutdown event; and in accordance with a determination that there is lubricant dilution, output an indication of the lubricant dilution.

In yet another aspect, a method for detecting lubricant dilution for a lubrication system is disclosed. The method includes: detecting a shutdown event of the lubrication system when one or more operating conditions associated with the lubrication system decreases below a shutdown event threshold; measuring lubricant pressure during the shutdown event; comparing the measured lubricant pressure to a lubricant dilution threshold determining whether the measured lubricant pressure is less than the lubricant dilution threshold; and in accordance with a determination that the measured lubricant pressure is less than the lubricant dilution threshold, determining lubricant dilution; and in accordance with a determination that there is lubricant dilution, outputting an indication of the lubricant dilution.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Both the foregoing general description and the following detailed description are exemplary and explanatory only and are not restrictive of the features, as claimed. As used herein, the terms "comprises," "comprising," "has," "having," "includes," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, unless stated otherwise, relative terms, such as, for example, "about," "substantially," and "approximately" are used to indicate a possible variation of ±10% in the stated value.

Figure 1:
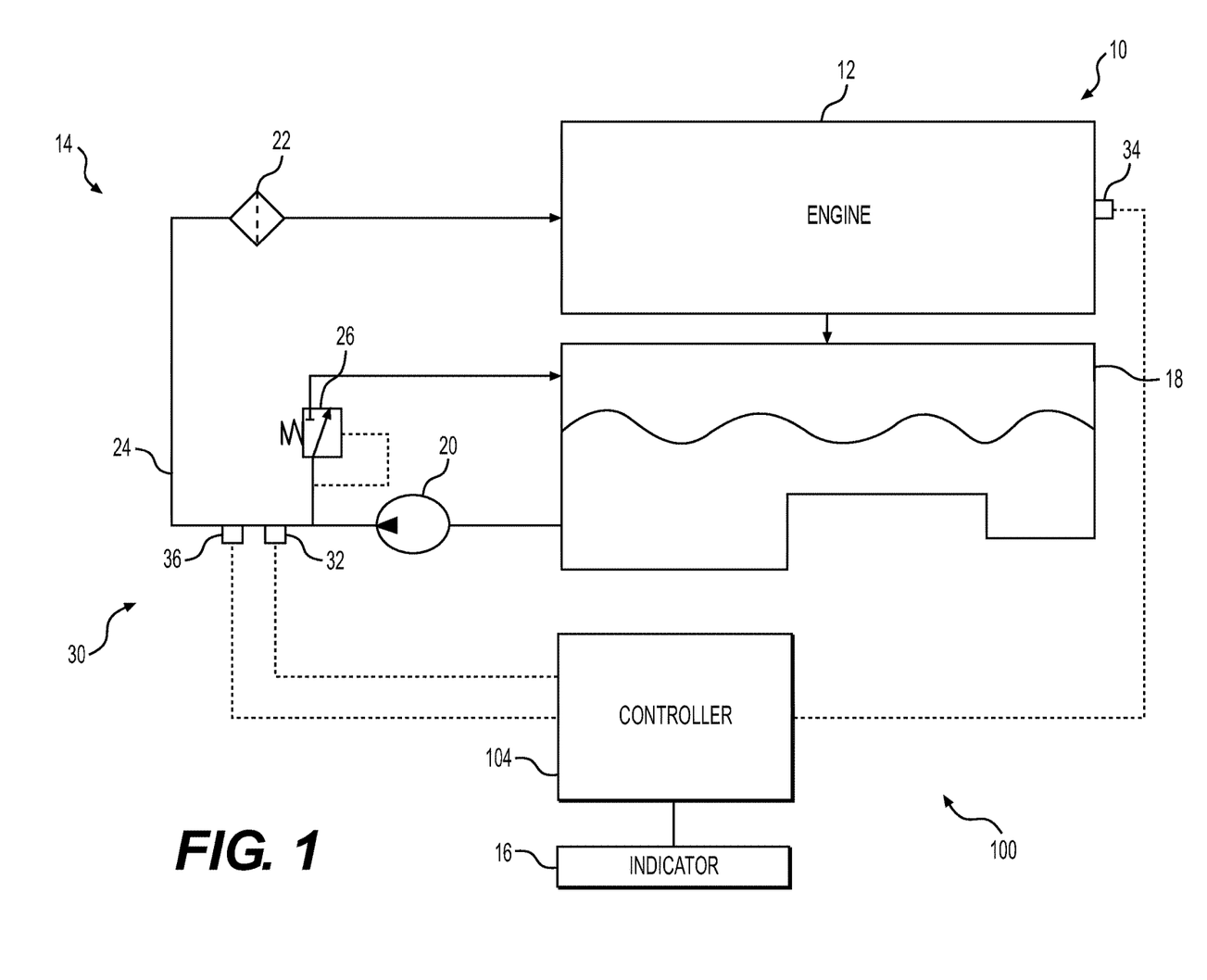
FIG. 1 is a schematic view of an engine system having a lubricant dilution detection system, according to aspects of the disclosure.

FIG. 1 illustrates a schematic view of an engine system 10 system having a lubricant dilution detection system 100. Engine system 10 includes an engine 12, such as an internal combustion engine. Engine 12 may include for example, a diesel engine, a gasoline engine, a dual fuel engine (e.g., an engine capable of running on both gaseous fuel and/or liquid fuel), or any other type of engine known in the art. Engine 12 may be used in power generator applications, mobile machines (e.g., vehicles), other types of heavy machinery or equipment, or the like. Operation of engine 12 may produce power. For example, engine 12 may include one or more cylinders (not shown) and a crankshaft (not shown) for providing power to a flywheel (not shown) or the like. As shown in FIG. 1, engine system 10 also includes a lubrication system 14, a lubricant dilution detection system 100, and an output indicator 16. Engine system 10 may include other components and/or systems, such as, for example, a transmission system and/or other mechanical systems including moving and/or rotating components.

Lubrication system 14 may include a lubricant supply 18, such as a lubricant pan, a pump 20, and a filter 22 in communication with each other via a lubricant supply line 24 (e.g., lubricant gallery). The lubricant may include oil or any other type of liquid lubricant known in the art. Pump 20 may include a mechanical pump for pressurizing fluid (e.g., lubricant) to generate flow of lubricant from lubricant supply 18 through lubrication system 14. For example, pump 20 may include a gear-type pump driven by gear trains from the crankshaft or other rotating components of engine 12. Further, pump 20 may be driven by other means and may include, for example, an electric driven pump, a hydraulic driven pump, and/or any other type of pump. Pump 20 may include a pressure regulator valve 26 for reducing and regulating a pressure of the lubricant exiting pump 20 and lowering the pressure to a predetermined level, as detailed further below. Valve 26 may receive pressure signals from lubricant supply line 24 (e.g., as shown by the dashed lines connected to valve 26), such that valve 26 is controllable by the pressure signals between an open position and a closed position for regulating the pressure at the predetermined level.

Lubricant supply line 24 may include a series of pipes or passageways for supplying lubricant from lubricant supply 18 to various components of engine 12. For example, lubrication system 14 may supply lubricant to the crankshaft, the pistons, a camshaft (not shown), bearings (not shown), and/or any other components of engine 12. Excess lubricant may drain back into lubricant supply 18. Filter 22 may remove particulates or other contaminants from the lubricant to prevent the particulates or contaminants from damaging components of engine 12. It is understood that lubrication system 14 may include any number and/or combination of valves or other components known in the art, such as one or more lubricant coolers (not shown), a scavenge pump (not shown), a pressure relief valve, and/or other types of filters (e.g., suction screen and/or centrifugal lubricant filter). Further, while the exemplary embodiment describes a lubrication system 14 for an engine 12, it is understood that aspects of the disclosure may be used for lubrication systems for any other type of mechanical system having moving and/or rotating components (e.g., transmission systems).

Output indicator 16 may indicate lubrication dilution in lubrication system 14, as detailed below. Output indicator 16 may include a display, a gauge, a light, a speaker, or the like. For example, output indicator 16 may indicate a value (numerical value, percentage, or the like) indicative of dilution of the lubricant in lubrication system 14 and/or may indicate (e.g., via a notification) when the lubricant is diluted. Indicator 16 may be located as part of engine system 10 (e.g., in an operator cab of a mobile machine) and/or may be located remote from engine system 10. While only a single output indicator 16 is described herein, it is understood that output indicator 16 may include one or more indicators and may include any type of indicator for indicating lubricant dilution in lubrication system 14.

Lubricant dilution detection system 100 includes a controller 104, such as an engine control module (ECM), and a sensor system 30 connected to controller 104. Sensor system 30 may include one or more sensors for measuring operating conditions, such as pressure sensors, temperature sensors, flow sensors, speed sensors, or the like. For example, sensor system 30 may include a lubricant pressure sensor 32, an engine speed sensor 34, and/or a lubricant temperature sensor 36. Lubricant pressure sensor 32 may be located in lubricant supply line 24 downstream of pump 20 and may sense values indicative of a pressure of lubricant in lubrication system 14. Engine speed sensor 34 may be located at the crankshaft of engine 12 and may sense values indicative of engine speed. Engine speed sensor 34 may be located at any location of engine 12, such as, for example, a crank pulley, the flywheel, a camshaft, or on the crankshaft. Lubricant temperature sensor 36 may be located in lubricant supply line 24 downstream of pump 20 and may sense values indicative of a temperature of lubricant in lubrication system 14. For example, lubricant temperature sensor 36 may sense a temperature of the lubricant directly. In some embodiments, lubricant temperature sensor 36 may sense a temperature of coolant in a cooling system (not shown) of engine system 10. The temperature of the coolant may correspond to a temperature of the lubricant. As used herein, "lubricant temperature" may correspond to either, or both, of the lubricant temperature directly and/or the coolant temperature. It is understood that sensors 32, 34, 36 may include any type of sensor such as resistive sensors, inductive sensors, capacitive sensors, piezoelectric sensors, optical sensors, micro electro-mechanical system sensors, or the like. Further, sensor system 30 may include physical sensors and/or virtual sensors (e.g., sensors that determine a value indirectly by controller 104 based on other sensed values) and may include any number and/or combination of sensors as necessary for sensing or measuring operating conditions.

Figure 2:
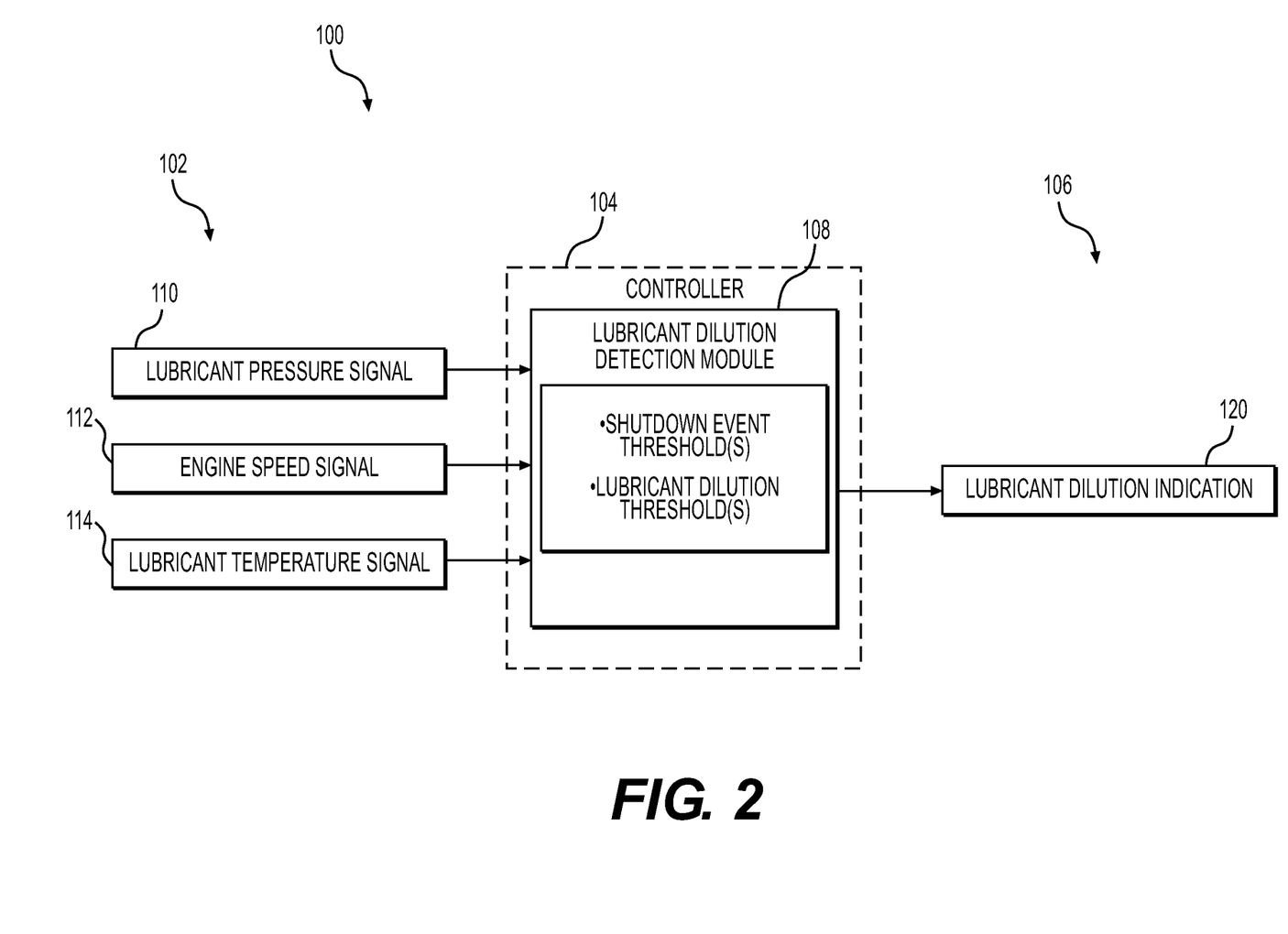
FIG. 2 is a schematic view of the exemplary lubricant dilution detection system for the engine system of FIG. 1.

FIG. 2 illustrates a schematic view of the exemplary lubricant dilution detection system 100 for operation and/or control of at least portions of engine system 10. System 100 may include inputs 102, controller 104, and outputs 106. Inputs 102 may include, for example, lubricant pressure signal 110 from pressure sensor 32, engine speed signal 112 from speed sensor 34, and lubricant temperature signal 114 from temperature sensor 36. Outputs 106 may include, for example, a lubricant dilution indication signal 120. Controller 104 may also receive other inputs (not shown) from other sensors or components of engine 12, such as, for example, a key off signal, and/or signals from sensors indicating one or more engine operating conditions. Controller 104 also includes a lubricant dilution detection module 108. Lubricant dilution detection module 108 may receive inputs 102, implement a method 300 for detecting dilution of lubricant in lubrication system 14 and control outputs 106, as described with reference to FIG. 3 below.

Controller 104 may embody a single microprocessor or multiple microprocessors that may include means for detecting dilution of lubricant in lubrication system 14. For example, controller 104 may include a memory, a secondary storage device, and a processor, such as a central processing unit or any other means for accomplishing a task consistent with the present disclosure. The memory or secondary storage device associated with controller 104 may store data and/or software routines that may assist controller 104 in performing its functions, such as the functions of method 300 of FIG. 3. Further, the memory or secondary storage device associated with controller 104 may also store data received from the various inputs 102 associated with lubricant dilution detection system 100. Numerous commercially available microprocessors can be configured to perform the functions of controller 104. It should be appreciated that controller 104 could readily embody a general machine controller capable of controlling numerous other machine functions. Further, controller 104, or portions thereof, may be located remote from engine system 10. Various other known circuits may be associated with controller 104, including signal-conditioning circuitry, communication circuitry, hydraulic or other actuation circuitry, and other appropriate circuitry.

Controller 104 may also include stored values for use by module 108. For example, the stored values may include shutdown event thresholds and lubricant dilution thresholds. Shutdown event thresholds may include one or more thresholds for various operating conditions (e.g., engine speed, fuel pump flow rate, air intake, etc.) of engine system 10 that indicate a shutdown event for engine system 10, and thus indicate a shutdown event for lubrication system 14. For example, the shutdown event thresholds may include an engine speed threshold (e.g., 850 RPM). When one or more operating conditions (e.g., engine speed) reduce below the respective shutdown event threshold, controller 104 may determine lubrication system 14 (e.g., engine 12) is shutting down. Shutdown may be commanded by an operator of engine 12 (e.g., by a key off event) and/or may be commanded by controller 104 (e.g., by one or more operating conditions exceeding a threshold).

Figure 4A:
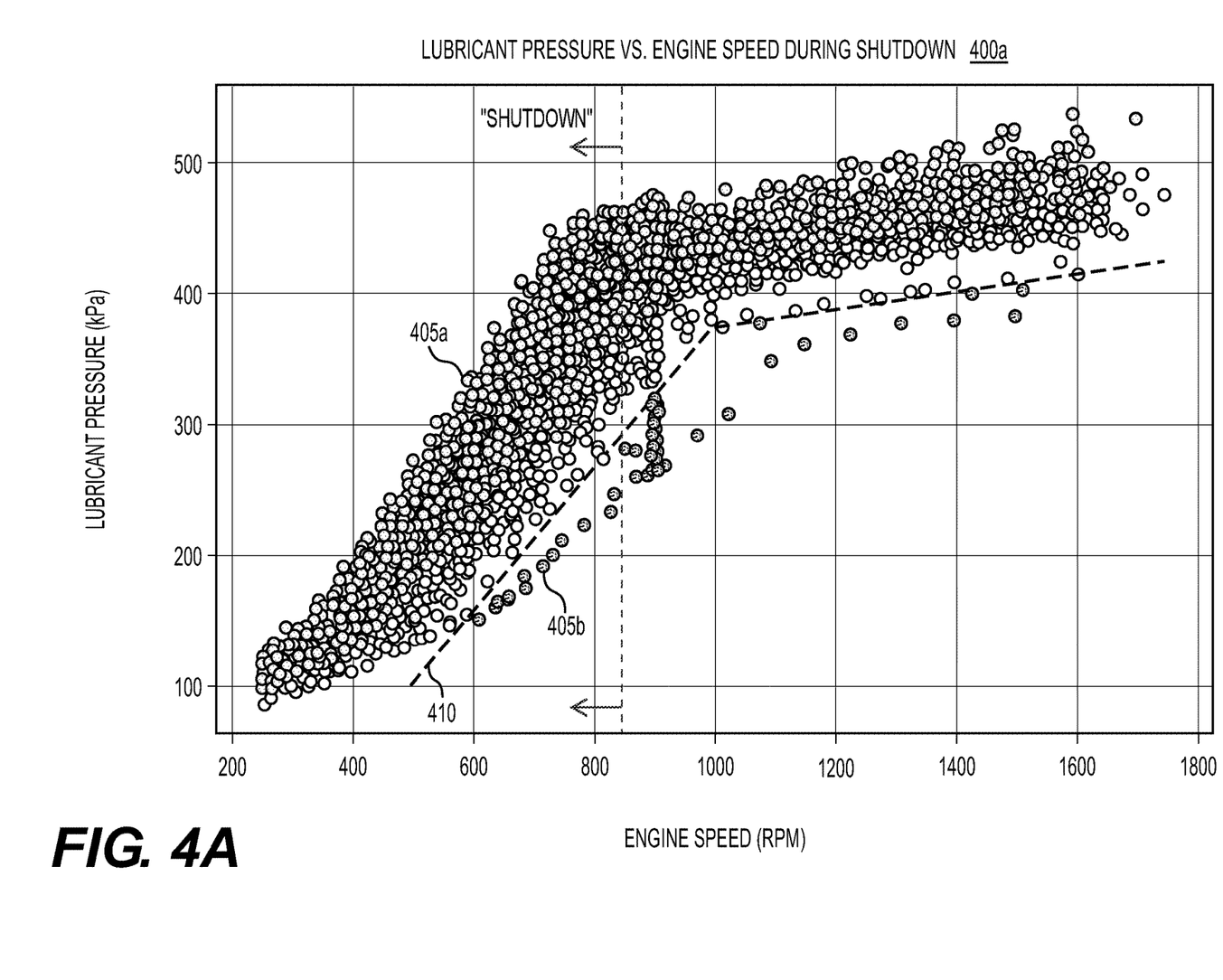
FIGS. 4A and 4B are plots of lubricant pressure versus engine speed during shutdown, according to one or more embodiments.
Figure 4B:
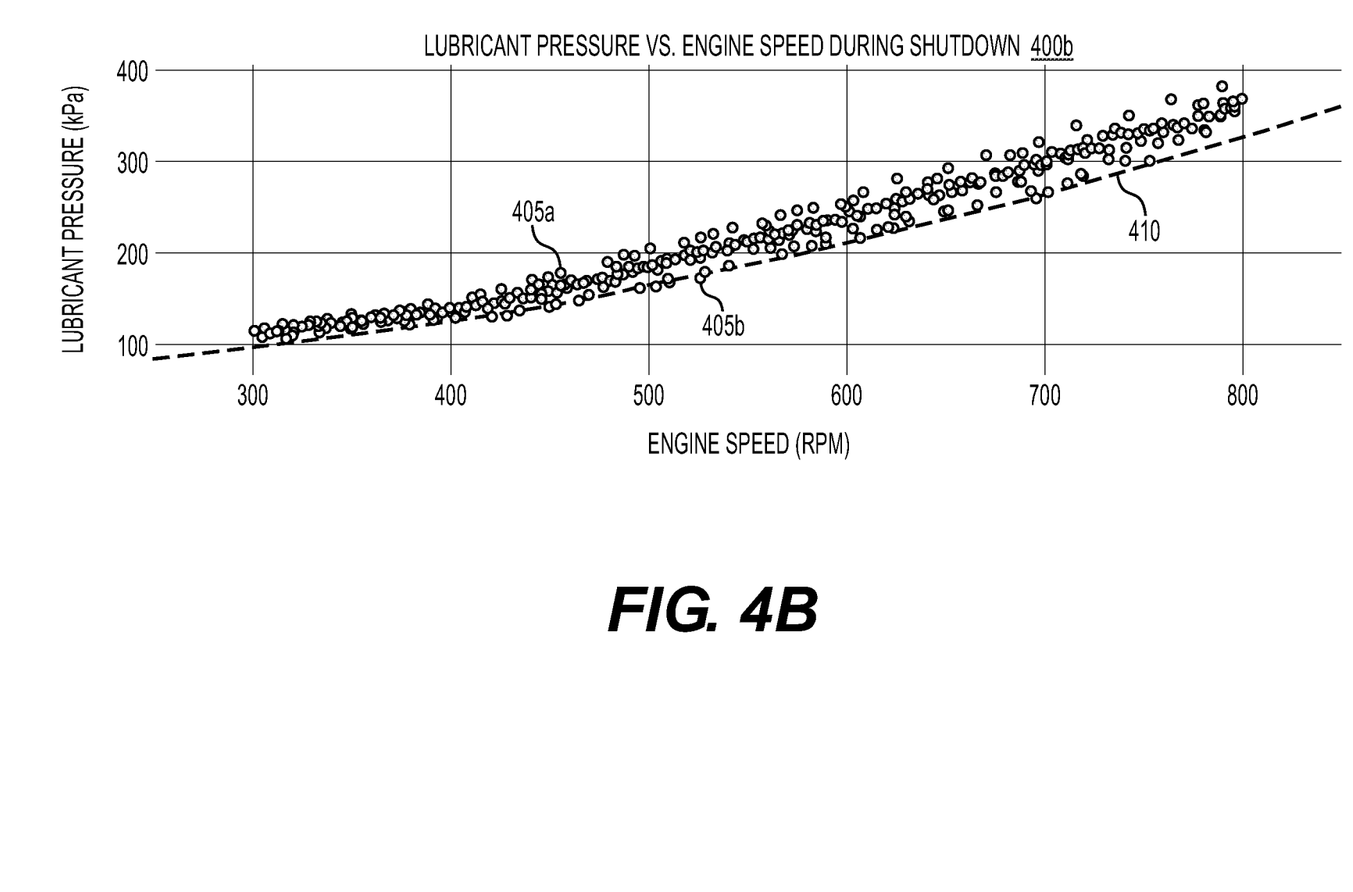

The lubricant dilution thresholds may include one or more thresholds for indicating lubricant dilution for lubrication system 14. For example, the lubricant dilution thresholds may include one or more lubricant dilution pressure thresholds. The one or more lubricant dilution pressure thresholds may include a variable threshold as a function of engine speed during a shutdown event (as shown in FIGS. 4A and 4B by thresholds 410). For example, the one or more lubricant dilution pressure thresholds may include different pressure thresholds for different engine speeds during a shutdown event provided in a map or lookup table. The information used to derive the values of the map or lookup table may be determined by empirical analysis. Such empirical data may be obtained, for example, by operating a test engine system 10 under predetermined conditions (e.g., under particular operating conditions) during, for example, bench testing. For example, the threshold values may be correlated to the values of the engine operating conditions (e.g., engine speed). It is understood that the map or lookup table may provide the values of the lubricant dilution pressure threshold as a function of any type of input as desired, such as other operating conditions (e.g., values indicative of lubricant temperature).

The lubricant dilution thresholds may also include ranges for various operating conditions during a shutdown event for limiting the data points used in the measurements that are compared to the thresholds. For example, the ranges may include an engine speed range (e.g., 250-850 RPM), a lubricant pressure range (e.g., 50-600 kPa), and/or a lubricant (e.g., or coolant) temperature range (e.g., 65-105° C., or 80-95° C.). Thus, any measured data points of lubricant pressure during which the respective operating conditions (e.g., engine speed, lubricant pressure, lubricant temperature) fall outside the respective ranges may be disregarded, such that noise in the data may be filtered out. Further, it is understood that the provided ranges are exemplary only, and the engine speed range, lubricant pressure range, and/or the lubricant temperature range may include any other range as necessary for a respective application.

Lubricant dilution indication signal 120 may include control of aspects of engine system 10. For example, lubricant dilution indication signal 120 may include controller 104 outputting a signal to display a value indicative of lubricant dilution in lubrication system 14 on output indicator 16 (e.g., on a display). Lubricant dilution indication signal 120 may also include controller 104 outputting an alert, such as a light, an audible alert, an alert on a display, or the like when there is lubricant dilution. The lubricant dilution indication signal 120 may also include mitigation or remediation recommendations. For example, module 108 may recommend service intervals, lubrication system tests, fuel system tests, and/or any other maintenance techniques for locating, mitigating, and/or remediating the cause of the lubricant dilution. Lubricant dilution indication signal 120 may also include controller 104 adjusting the engine system 10. For example, controller 104 may derate or shut down engine system 10 or portions thereof.

INDUSTRIAL APPLICABILITY

The disclosed aspects of the lubricant dilution detection system 100 of the present disclosure may be used in any lubrication system 14 that supplies pressurized lubricant.

Referring to FIG. 1, during the operation of engine system 10, engine 12 may drive pump 20 such that pump 20 may draw lubricant from lubricant supply 18. Pump 20 may thus provide pressurized lubricant out of pump 20 to components of engine 12 through supply line 24 such that the components of engine 12 are lubricated. For example, as engine speed increases, pump 20 speed may increase such that lubricant pressure increases. During operation of engine system 10, the pressurized lubricant may be regulated at a predetermined pressure in supply line 24 by valve 26 at certain engine speeds, as detailed above. For example, when the engine speed increases over a predetermined value, valve 26 may open proportionally such that the lubricant pressure does not exceed a predetermined pressure value (e.g., 600 kPa). In some instances, the lubricant may become diluted such that the viscosity of the lubricant decreases due to various causes, as detailed above. For example, coolant from a lubricant cooler of the lubrication system 14 and/or fuel (e.g., diesel) from one or more fuel injectors of the fuel system of the engine 12 may leak into the lubricant supply 18. The coolant and/or the fuel may have a lower viscosity than the lubricant such that the viscosity of the lubricant-coolant/fuel mixture is lower than the viscosity of the lubricant itself. When the lubricant is diluted, the components of the engine 12 may become damaged due the reduced lubrication ability of the lubricant. Further, as valve 26 regulates the lubricant pressure at relatively higher engine speeds, it may be difficult to detect lubricant dilution when valve 26 is open. For example, the lubricant pressure may build to the predetermined value to open valve 26 even if the lubricant is diluted. Therefore, lubricant dilution may not be adequately detected during relatively higher engine speeds when valve 26 is open. Further, in some types of engine systems, valve 26 may not close while the engine is operating (e.g., during an idle condition). Thus, as detailed below with reference to FIG. 3, lubricant dilution detection system 100 may detect lubricant dilution during shutdown events of engine system 10 when valve 26 is closed (e.g., at engine speeds less than 850 RPM).

Figure 3:
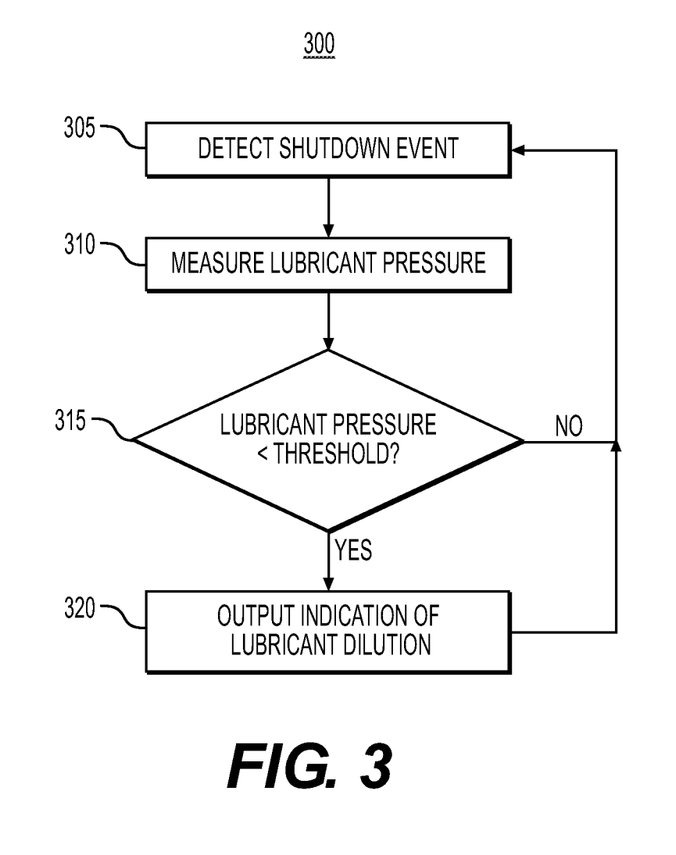
FIG. 3 provides a flowchart depicting an exemplary method for detecting dilution of a lubricant for the system of FIG. 1.

FIG. 3 illustrates a flowchart depicting an exemplary method 300 for detecting lubricant dilution for lubrication system 14. In step 305, module 108 may detect a shutdown event of lubrication system 14 (e.g., shutdown of engine system 10). For example, module 108 may receive a shutdown signal (e.g., key off or commanded by controller 104) and/or may otherwise measure engine speed and determine that the engine speed is decreasing below the predetermined shutdown threshold. As detailed above, module 108 may utilize other operating condition parameters and respective shutdown event thresholds (e.g., engine speed, fuel pump flow rate, air intake, etc.). In accordance with a determination that a respective operating condition decreases below the respective shutdown event threshold, module 108 may determine a shutdown event of lubrication system 14. It is understood that module 108 may detect a shutdown event of lubrication system 14 by any other method known in the art.

In step 310, when module 108 has detected a shutdown event of lubrication system 14, module 108 may measure lubricant pressure of lubrication system 14 during the shutdown event. For example, controller 104 may receive the lubricant pressure signal 110 and determine, or otherwise derive, the lubricant pressure of lubrication system 14. Module 108 may also determine a rate of lubricant pressure change over time based on the lubricant pressure signal 110. Further, eventually the lubricant pressure will approach and decrease to zero when lubrication system 14 is completely shut down (e.g., when the shutdown event is complete). Therefore, module 108 may limit the measurement window for method 300 when engine speed is in the engine speed range (e.g., between 250-850 RPM), as detailed above.

In step 315, module 108 may determine whether the measured lubricant pressure is less than a threshold (e.g., the lubricant dilution threshold based on operating conditions, as detailed above). For example, when there is no dilution, or negligible dilution, and the lubrication system 14 shuts down, the lubricant pressure will be above the respective lubricant dilution threshold for a respective operating condition (e.g., engine speed). Thus, when the measured lubricant pressure is greater than or equal to the threshold (Step 315: NO), module 108 may repeat the method 300 and continue to detect shutdown events (step 305).

When the lubricant is diluted, the lubricant pressure may decrease below the respective lubricant dilution threshold for a respective operating condition (e.g., engine speed) during the shutdown. Thus, in step 320, in accordance with a determination that the measured lubricant pressure is less than the threshold (Step 315: YES), module 108 may output an indication of lubricant dilution. For example, module 108 may display the indication of the lubricant dilution on output indicator 16 (e.g., on a display and/or as a notification, such as a light, an audible alert, an alert on a display, etc.). Module 108 may then repeat the method 300 and continue to detect shutdown events (step 305). Further, module 108 may store the indication of lubricant dilution (e.g., as a flag), such that module 108 may indicate lubricant dilution when lubrication system 14 is started up again. Module 108 may also generate recommendations for mitigating the lubricant dilution and output the recommendations (e.g., via output indicator 16).

In some embodiments, module 108 may store values or instances of the measured lubricant pressure during a plurality of shutdown events. For example, module 108 may detect several different shutdown events and store values of the measured lubricant pressure. Referring to FIGS. 4A and 4B, module 108 may generate a plot 400a, 400b of the measured lubricant pressure for the different shutdown events over time. For example, FIG. 4A provides a plot 400a of lubricant pressure versus engine speed during shutdown according to a first embodiment. Similarly, FIG. 4B provides a plot 400b of lubricant pressure versus engine speed during shutdown according to a second embodiment. Plots 400a, 400b may include a graphical representation of various data points 405a, 405b of the measured lubricant pressure for various engine speeds. Further, the dashed line indicates the lubricant dilution thresholds 410 for the various engine speeds. As shown in FIG. 4A, the lubricant dilution thresholds 410 may be substantially linear as engine speed decreases during a shutdown event (e.g., engine speed less than 850 RPM, as indicated by the vertical dashed line in FIG. 4A). However, in embodiments where pump 20 is driven by engine 12 (e.g., the crankshaft), there is a second order relationship between lubricant pressure out of pump 20 and engine speed. For example, a delay may exist between engine speed decreasing and pump 20 speed decreasing, thus causing a delay in lubricant pressure decreasing as engine speed decreases. Accordingly, the relationship between lubricant pressure and engine speed may not be exactly linear. Thus, as shown in FIG. 4B, the lubricant dilution thresholds 410 are not exactly linear as engine speed decreases. For example, the thresholds 410 may be exponential or may include another type of relationship between lubricant pressure and engine speed. Thus, lubricant dilution may exist when one or more data points 405b fall below the respective lubricant dilution threshold 410 for a respective engine speed during the shutdown. As detailed above, it is understood that plots 400a, 400b may include lubricant pressure versus other operating conditions other than engine speed, such as, for example, lubricant temperature or any other operating condition.

Further, to reduce or eliminate false triggers of lubricant dilution detection, module 108 may include one or more predetermined ranges for various operating conditions. For example, module 108 may consider data points 405a, 405b of the measured lubricant pressure that are measured when a value indicative of engine speed is between 250-850 RPM, a value indicative of lubricant temperature (e.g., as measured from lubricant temperature signal 114) is between 65-105° C. (or 80-95° C.), and/or a value indicative of lubricant pressure is between 50-600 kPa. Thus, module 108 may disregard or otherwise eliminate data points of the measured lubricant pressure when the respective operating conditions are outside the respective ranges. To further reduce or eliminate false triggers of lubricant dilution detection, module 108 may also include debounce conditions. For example, the debounce conditions may include predetermined thresholds for an amount of time (e.g., 3 seconds) the measured lubricant pressure is less than the lubricant dilution thresholds. Similarly, module 108 may also include an amount of data points 405b that required to be less than the lubricant dilution thresholds as a function of the total amount of data points 405a, 405b. For example, if 3 out of 15 data points fall below the lubricant dilution thresholds, module 108 may determine lubricant dilution.

Lubricant dilution detection system 100 may provide an indication of lubricant dilution in lubrication system 14. For example, lubricant dilution detection system 100 may detect lubricant dilution due to, for example, fuel leaks in a fuel system of engine 12, coolant leaks from a lubricant cooler, age of the lubricant, and/or any other causes of dilution. Further, by detecting lubricant dilution during shutdown events, lubricant dilution detection system 100 may ensure that valve 26 is closed such that system 100 may more adequately detect lubricant dilution. Accordingly, lubricant dilution detection system 100 may more accurately or adequately detect lubricant dilution in lubrication system 14 and proactively alert a user (e.g., operator, technician, etc.) so that the user may repair and/or replace the respective component to mitigate the lubrication dilution.

It will be apparent to those skilled in the art that various modifications and variations can be made to the disclosed system without departing from the scope of the disclosure. Other embodiments of the system will be apparent to those skilled in the art from consideration of the specification and practice of the system disclosed herein. It is intended that the specification and examples be considered as exemplary only, with a true scope of the disclosure being indicated by the following claims and their equivalents.

What is claimed is:

1. A method for detecting lubricant dilution for a lubrication system, comprising:
   detecting a shutdown event of the lubrication system;
   measuring lubricant pressure during the shutdown event;
   determining lubricant dilution based on the measured lubricant pressure during the shutdown event; and
   in accordance with a determination that there is lubricant dilution, outputting an indication of the lubricant dilution.

2. The method of claim 1, wherein detecting the shutdown event includes detecting a key off signal or a shutdown command signal.

3. The method of claim 1, wherein detecting the shutdown event includes detecting that an engine speed decreases below a threshold.

4. The method of claim 1, further including:
   determining lubricant dilution based on the measured lubricant pressure during a plurality of shutdown events.

5. The method of claim 1, wherein determining lubricant dilution includes:
   comparing the measured lubricant pressure to a threshold;
   determining whether the measured lubricant pressure is less than the threshold; and
   in accordance with a determination that the measured lubricant pressure is less than the threshold, determining lubricant dilution.

6. The method of claim 5, wherein the threshold is a variable threshold based on engine speed.

7. The method of claim 6, further including:
   determining lubricant dilution when the measured lubricant pressure is less than the threshold for a predetermined amount of time.

8. The method of claim 1, further including determining lubricant dilution based on the measured lubricant pressure during the shutdown event when a value indicative of lubricant temperature is between 65-105° C.

9. The method of claim 1, wherein outputting an indication of the lubricant dilution includes:
   generating recommendations for mitigating the lubricant dilution; and
   outputting the recommendations.

10. A lubricant dilution detection system, comprising:
    a lubrication system;
    a sensor for measuring lubricant pressure in the lubrication system; and
    a controller configured to:
      detect a shutdown event of the lubrication system;
      measure lubricant pressure during the shutdown event;
      determine lubricant dilution based on the measured lubricant pressure during the shutdown event; and
      in accordance with a determination that there is lubricant dilution, output an indication of the lubricant dilution.

11. The system of claim 10, wherein detecting the shutdown event includes the controller configured to detect a key off signal or a shutdown command signal.

12. The system of claim 10, wherein detecting the shutdown event includes the controller configured to detect that an engine speed decreases below a threshold.

13. The system of claim 10, wherein the controller is further configured to:
    determine lubricant dilution based on the measured lubricant pressure during a plurality of shutdown events.

14. The system of claim 10, wherein the controller is further configured to:
    compare the measured lubricant pressure to a threshold;
    determine whether the measured lubricant pressure is less than the threshold; and
    in accordance with a determination that the measured lubricant pressure is less than the threshold, determine lubricant dilution.

15. The system of claim 14, wherein the threshold is a variable threshold based on engine speed.

16. The system of claim 15, wherein the controller is further configured to:
    determine lubricant dilution when the measured lubricant pressure is less than the threshold for a predetermined amount of time.

17. The system of claim 10, wherein the controller is further configured to:
    determine lubricant dilution based on the measured lubricant pressure during the shutdown event when a value indicative of lubricant temperature is between 65-105° C.

18. The system of claim 10, wherein outputting an indication of the lubricant dilution includes the controller configured to:
    generate recommendations for mitigating the lubricant dilution; and
    output the recommendations on the output indicator.

19. A method for detecting lubricant dilution for a lubrication system, comprising:
    detecting a shutdown event of the lubrication system when one or more operating conditions associated with the lubrication system decreases below a shutdown event threshold;
    measuring lubricant pressure during the shutdown event;
    comparing the measured lubricant pressure to a lubricant dilution threshold
    determining whether the measured lubricant pressure is less than the lubricant dilution threshold; and
    in accordance with a determination that the measured lubricant pressure is less than the lubricant dilution threshold, determining lubricant dilution; and
    in accordance with a determination that there is lubricant dilution, outputting an indication of the lubricant dilution.

20. The method of claim 19, wherein the lubricant dilution threshold is a variable threshold based on engine speed.

* * * * *